(12) United States Patent
Gass

(10) Patent No.: US 8,363,646 B2
(45) Date of Patent: Jan. 29, 2013

(54) APPLICATION SERVER FOR DISPATCHING PHYSIOLOGICAL SIGNALS IN A HOSPITAL, IN REAL TIME

(75) Inventor: Raymond Gass, Bolsenheim (FR)

(73) Assignee: Alcatel Lucent, Paris (FR)

( * ) Notice: Subject to any disclaimer, the term of this patent is extended or adjusted under 35 U.S.C. 154(b) by 0 days.

(21) Appl. No.: 13/003,601

(22) PCT Filed: Jul. 10, 2009

(86) PCT No.: PCT/EP2009/058810
§ 371 (c)(1),
(2), (4) Date: Jul. 27, 2011

(87) PCT Pub. No.: WO2010/004026
PCT Pub. Date: Jan. 14, 2010

(65) Prior Publication Data
US 2011/0274013 A1    Nov. 10, 2011

(30) Foreign Application Priority Data
Jul. 11, 2008 (EP) ..................... 08305394

(51) Int. Cl.
*H04L 12/66* (2006.01)
(52) U.S. Cl. .......................... 370/352; 370/392
(58) Field of Classification Search .................. None
See application file for complete search history.

(56) References Cited

U.S. PATENT DOCUMENTS

| | | | |
|---|---|---|---|
| 5,025,809 A | 6/1991 | Johnson et al. | |
| 6,705,990 B1 * | 3/2004 | Gallant et al. | 600/300 |
| 2004/0030585 A1 | 2/2004 | Sariel | |
| 2004/0170154 A1 | 9/2004 | Carter et al. | |
| 2005/0265267 A1 | 12/2005 | Hwang | |
| 2008/0004904 A1 * | 1/2008 | Tran | 705/2 |
| 2011/0110276 A1 * | 5/2011 | Rae | 370/260 |

FOREIGN PATENT DOCUMENTS
WO    WO 02/27640 A    4/2002

OTHER PUBLICATIONS

International Search Report for PCT/EP2009/058810 dated Aug. 19, 2009.
European Search Report for EP 08305394 dated Jan. 16, 2009.
Mehran Nekuii, Student Member, IEEE, and Mojtaba Atarodi, Member, IEEE, "A Fast Converging Algorithm for Network Echo Cancellation," IEEE Signal Processing Letters, vol. 11, No. 4, pp. 427-430, Apr. 2004.
Eberhard Hansler and Gerhard Schmidt, "Acoustic Echo and Noise Control A Practical Approach," published by John Wiley & Sons, Inc., entire book, 2004.

* cited by examiner

Primary Examiner — Duc C Ho
(74) Attorney, Agent, or Firm — Fay Sharpe LLP

(57) ABSTRACT

An application server is provided for dispatching physiological signals in a hospital, in real time. Suitably, the hospital includes a local area network infrastructure with a virtual local area network supporting a voice over IP telephony application. The server comprises: means for receiving packets containing samples of a physiological signal via a first terminal connected to the virtual local area network, means for de-encapsulating a received packet containing samples of the physiological signal, at the real time transport protocol level, means for creating a second packet containing samples of the physiological signal, and forwarding the second packet back at least to the first terminal.

10 Claims, 8 Drawing Sheets

FIG_2

FIG_3

FIG_4

FIG_5

FIG_7
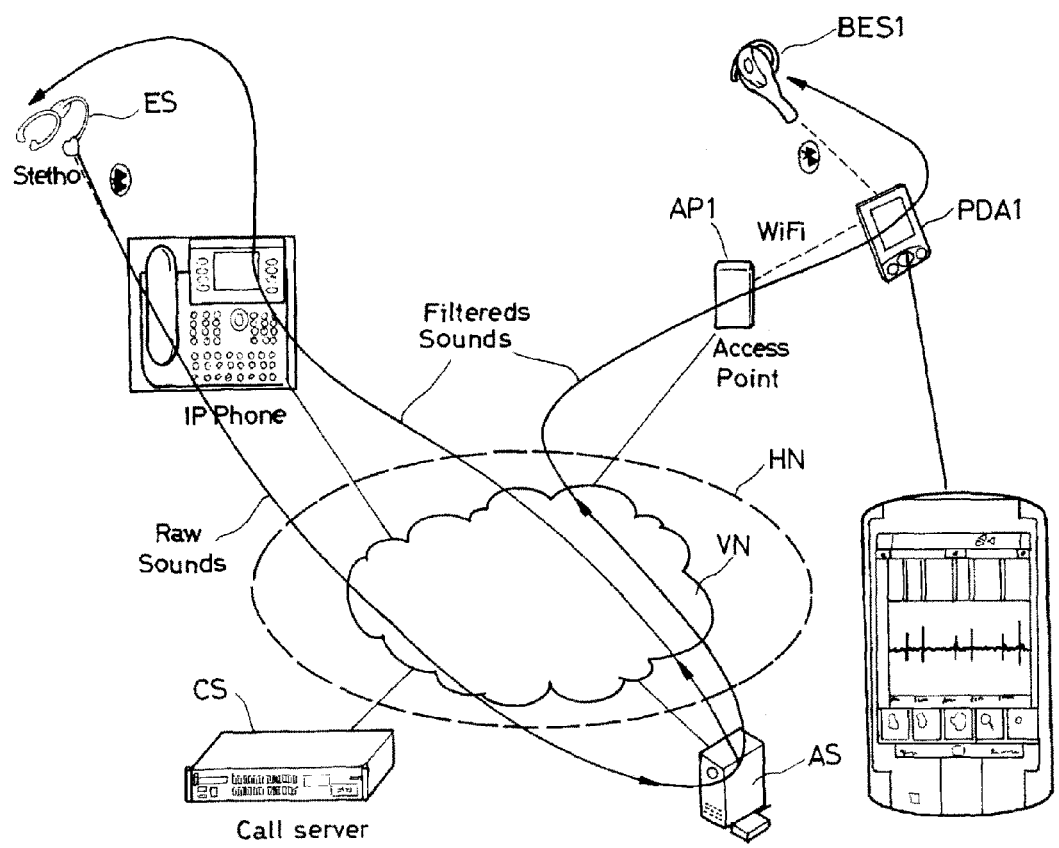

FIG_8
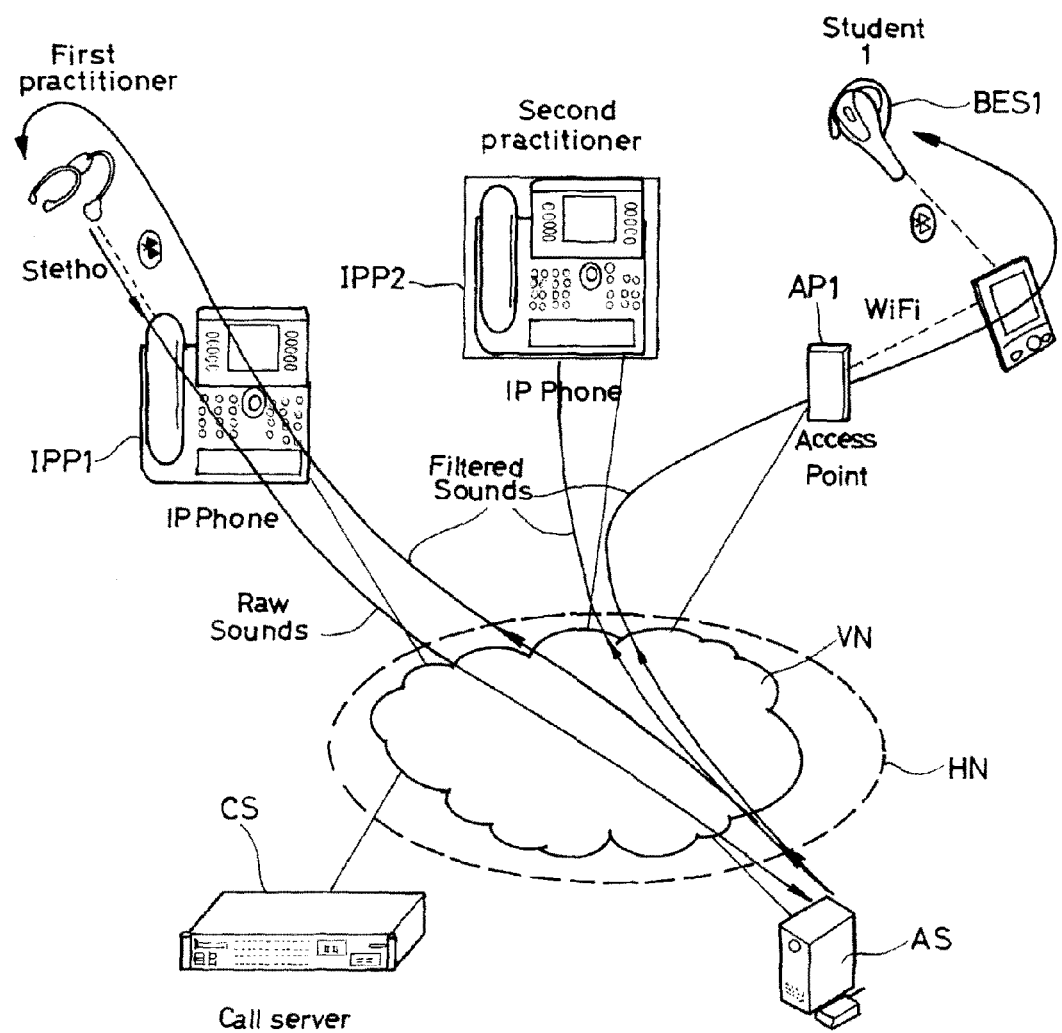

APPLICATION SERVER FOR DISPATCHING PHYSIOLOGICAL SIGNALS IN A HOSPITAL, IN REAL TIME

BACKGROUND OF THE INVENTION

1. Field of the Invention

The invention relates to an application server for dispatching physiological signals in a hospital, in real time. These signals may be auscultation sounds, electrocardiograms, electro-encephalograms, etc.

One of the uses of this application server is the teaching of auscultation to medicine students in a hospital. Auscultation consists in listening to sounds from the organism, in particular heart and lungs. Classically a medicine professor teaches auscultation in a patient's bedroom, by describing to students, what he/she is hearing. Then, each student auscultates the patient with his/her own stethoscope. He/she tries to find the right place where to put the chestpiece of the stethoscope, and tries to hear what the professor described. On one hand, this is quite unpleasant to the patient and on the other hand, this is not an objective way of teaching auscultation, this is not what is called today "evidence based medicine".

Some methods for auscultation teaching use recorded auscultation sounds, on cassettes or compact discs, but these methods are not as efficient as live capturing of auscultation sounds in real time on a chosen patient, together with relevant comments and description provided by an experienced practitioner. Some manufacturers provide additional listening units that make it possible to connect several headsets to a personal computer processing the auscultation sounds, so that several students are in a position to listen simultaneously to the same sounds. But this is a local operation limited to the lengths of the wires or tube of the headsets. This is not applicable to remote operation over networks such as legacy telephone networks, or cellular infrastructure, or over Internet.

In the existing solutions, when a practitioner wants to get a second opinion about a patient, he/she must request a colleague to come to the patient's room because there is no easy way to communicate the auscultation sounds to a colleague. When a practitioner wants to store a phonocardiogram, an electrocardiogram, an electro-encephalograms, in the patient's medical file, there is no easy way to send it to a central database connected to the hospital infrastructure and that stores the patients' files.

2. Description of the Prior Art

There exist electronic stethoscopes of the type comprising a microphone, electronic sound processing means, and sound reproducing means, such as a loudspeaker or headphones. An electronic stethoscope gives the possibility of active amplification and filtering to any desired degree. The output of an electronic stethoscope can be linked to a personal computer or a personal digital assistant for analyzing and displaying waveforms, for instance a phonocardiogram.

For teaching auscultation, an electronic stethoscope can be linked to a loudspeaker or a plurality of headphones to enable a plurality of students to listen to the auscultation sounds and to the professor's comments in real time. However this way of teaching auscultation implies to gather the students near the stethoscope, i.e. around the patient's bed. This is also unpleasant to the patient. It would be more comfortable for the patient if the professor was alone with the patient, and if the students could stay and listen in another room, or several other rooms.

One could consider connecting an electronic stethoscope to the telecommunication network of a hospital for dispatching an auscultation signal to a plurality of students outside the patient's bedroom. However there arise some difficulties inherent to the telecommunication networks in hospitals. Nowadays such a network is based on the Internet Protocol, and is generally separated in two parts: one supporting data, and one supporting telephony. The access to the part supporting data is forbidden for protecting the security of confidential data. The part supporting telephony is at least one virtual local area network (VLAN) supporting voice over IP (VOIP), and it is more easily accessible. However safety means prevent the multicasting of a signal to several destinations.

Thus, there is a need to provide a technical solution for dispatching a physiological signal to a plurality of destinations via the telecommunication network of a hospital.

This can be solved by the application server according to the invention.

SUMMARY OF THE INVENTION

The aim of the invention is to provide an application server for the connection of streaming mode medical devices (ECG, EEG, heart or lung auscultation, spirometer) in the local area network or wide area network of a hospital, with the goal of
- providing real time acoustic and visual feedback inside the room of the patient, during an auscultation for instance;
- offering secured multipoint transmission of an auscultation signal for the purposes of teaching several students with simultaneous listening of auscultation sounds together with visualization of the sounds;
- enabling access to a second experienced practitioner via real-time communications over legacy infrastructure, for a second opinion;
- automatic storage of streaming-mode signals together with preliminary comments for further diagnostic setting;
- secured and confidential access to previous records for a patient.

The object of the invention is an application server for dispatching physiological signals in a hospital, in real time, this hospital comprising a local area network infrastructure with a virtual local, area network supporting voice over IP telephony application; characterized in that it comprises:
- means for receiving packets containing samples of a physiological signal via a first terminal connected to the virtual local area supporting voice over IP,
- means for de-encapsulating a received packet containing samples of said physiological signal, at the real time transport protocol level,
- means for creating a second packet containing samples of said physiological signal, and forwarding the second packet back at least to the first terminal.

Thanks to this application server, physiological signals such as auscultation sounds and waveforms, electrocardiograms, electro-encephalograms, etc, can be dispatched to various destinations, in real time, via the telecommunication network of the hospital, because it comprises means for de-encapsulating a received packet containing samples of a physiological signal, at the real time transport protocol level, and means for creating a second packet containing samples of said physiological signal, and forwarding this second packet at least to the first terminal, and possibly to other terminals connected to the VLAN supporting the VOIP, i.e. without using the part, of the hospital network, that is supporting the transfer of data.

According to a preferred embodiment of the server according to the present invention, it further comprises means for processing the samples of a received physiological signal, for instance in order to enhance this physiological signal; and the means for creating a second packet are fit for inserting, into a second packet, processed samples supplied by said means for processing.

Thanks to the processing power of the application server, this server can send back to the practitioner an enhanced physiological signal, for instance filtered auscultation sounds or waveforms calculated by the server, that are more valuable for diagnostic.

According to a peculiar embodiment, means for creating a second packet comprise means for creating a source address and a destination address by permuting the source address and the destination address of said first packet, at the real time transport protocol level.

This embodiment has the advantage of quickly determining a destination address, because permuting the source address and the destination address of said first packet, at the real time transport protocol level, is a simple operation.

According to a peculiar embodiment of the server according to the present invention, it further comprises means for creating a third packet containing samples of said first packet, and forwarding the third packet to at least a second terminal connected to the virtual local area network supporting voice over IP, by creating a point to point flow for each destination terminal.

This embodiment has the advantage of dispatching a same physiological signal to a plurality of terminals without using a multicast address, which is generally forbidden by security means in a hospital.

According to a peculiar embodiment of the server according to the present invention, it further comprises means for processing the samples of a received physiological signal; and said means for creating a third packet containing samples of said received physiological signal are fit for inserting, into a third packet, processed samples supplied by said means for processing.

Thanks to the processing power of the application server, this server can dispatch enhanced physiological signals to a plurality of students or practitioners; for instance filtered auscultation sounds or waveforms calculated by the server, that are more valuable for diagnostic.

Other features and advantages of the present invention will become more apparent from the following detailed description of embodiments of the present invention, when taken in conjunction with the accompanying drawings.

BRIEF DESCRIPTION OF THE DRAWINGS

In order to illustrate in detail features and advantages of embodiments of the present invention, the following description will be with reference to the accompanying drawings. If possible, like or similar reference numerals designate the same or similar components throughout the figures thereof and description, in which:

FIG. 7 illustrates the use of this embodiment of the application server for displaying a phonocardiogram on a student's personal digital assistant during an auscultation lesson.

FIG. 8 illustrates the use of this embodiment of the application server for consulting a second experienced practitioner during an auscultation lesson.

DETAILED DESCRIPTION OF THE PREFERRED EMBODIMENTS

Figure 1:
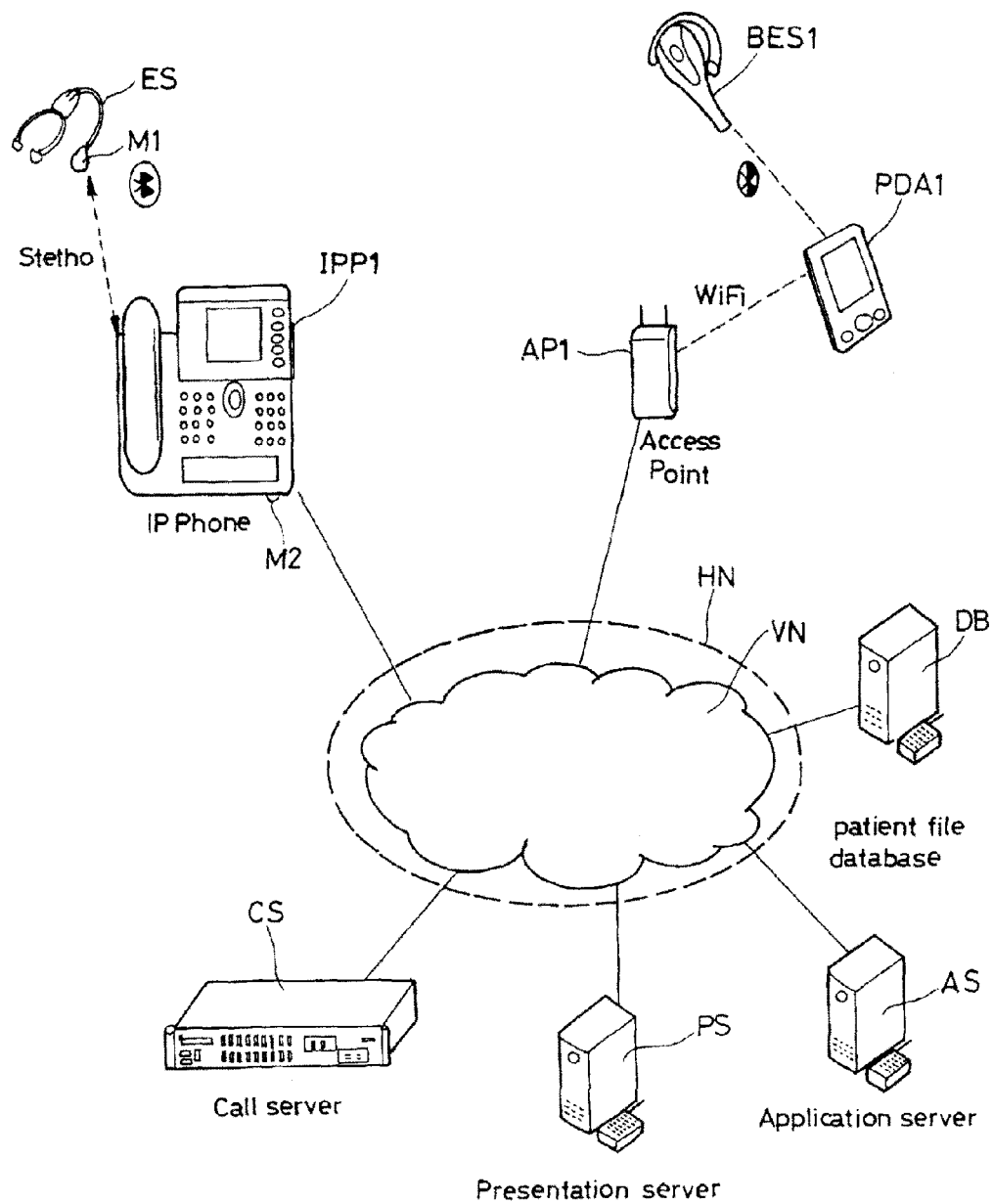
FIG. 1 is a block diagram showing an exemplary hospital local area network offering voice over IP telephony application, and comprising an embodiment of the application server according to the invention.

FIG. 1 is a block diagram showing an exemplary hospital local area network HN that comprises:
- A voice dedicated VLAN, VN, using the IP protocol family to route streaming packets containing voice samples. It is also used for streaming packets containing samples of physiological signals.
- A call server CS linked to the voice dedicated VLAN, VN, for establishing voice over IP communications between terminals linked to this VLAN.
- Wi-Fi access points, such as the access point AP1, linked to the voice dedicated VLAN, VN. They enable users to connect Wi-Fi terminals to the hospital network HN. For instance, a personal digital assistant PDA1 is connected to this access point AP1, while a Bluetooth ear set BES1 is connected to this personal digital assistant PDA1 by a Bluetooth link. The user of this equipment can place phone calls on the voice dedicated VLAN, VN, but he/she can also listen to an auscultation lesson, and look at auscultation waveforms on the display of the personal digital assistant PDA1, as it will be described below.
- IP phones, such as the IP phone IPP1, placed at patients' bedsides. Each of these IP phones comprises a screen that can display alphanumeric characters as well as a picture. Each of these IP phones also comprises a Bluetooth interface that enables to connect an audio device bidirectionally to the voice dedicated VLAN, VN. A cordless digital stethoscope ES can be connected to the IP phone IPP1 via this Bluetooth interface for sending samples of auscultation sounds through the voice dedicated VLAN, VN.
- A presentation server PS.
- A patient file database DB.
- An embodiment AS of the application server according to the invention, that can dispatch physiological signals, in particular dispatch auscultation sounds for:
  - sending auscultation sounds back to the headset of the electronic stethoscope ES after processing them in order to enhance sound characteristics that are valuable for a diagnostic,
  - teaching auscultation to distant students, via terminals connected to the voice dedicated VLAN, VN,
  - recording auscultation sounds into the patient file database DB,
  - consulting a distant experienced practitioner via a terminal connected to the voice dedicated VLAN, VN.

A terminal connected to the voice dedicated VLAN, VN, may be an IP phone of the hospital, but it may also be any distant VOIP terminal connected via any IP supporting network, wired or wireless.

Figure 2:
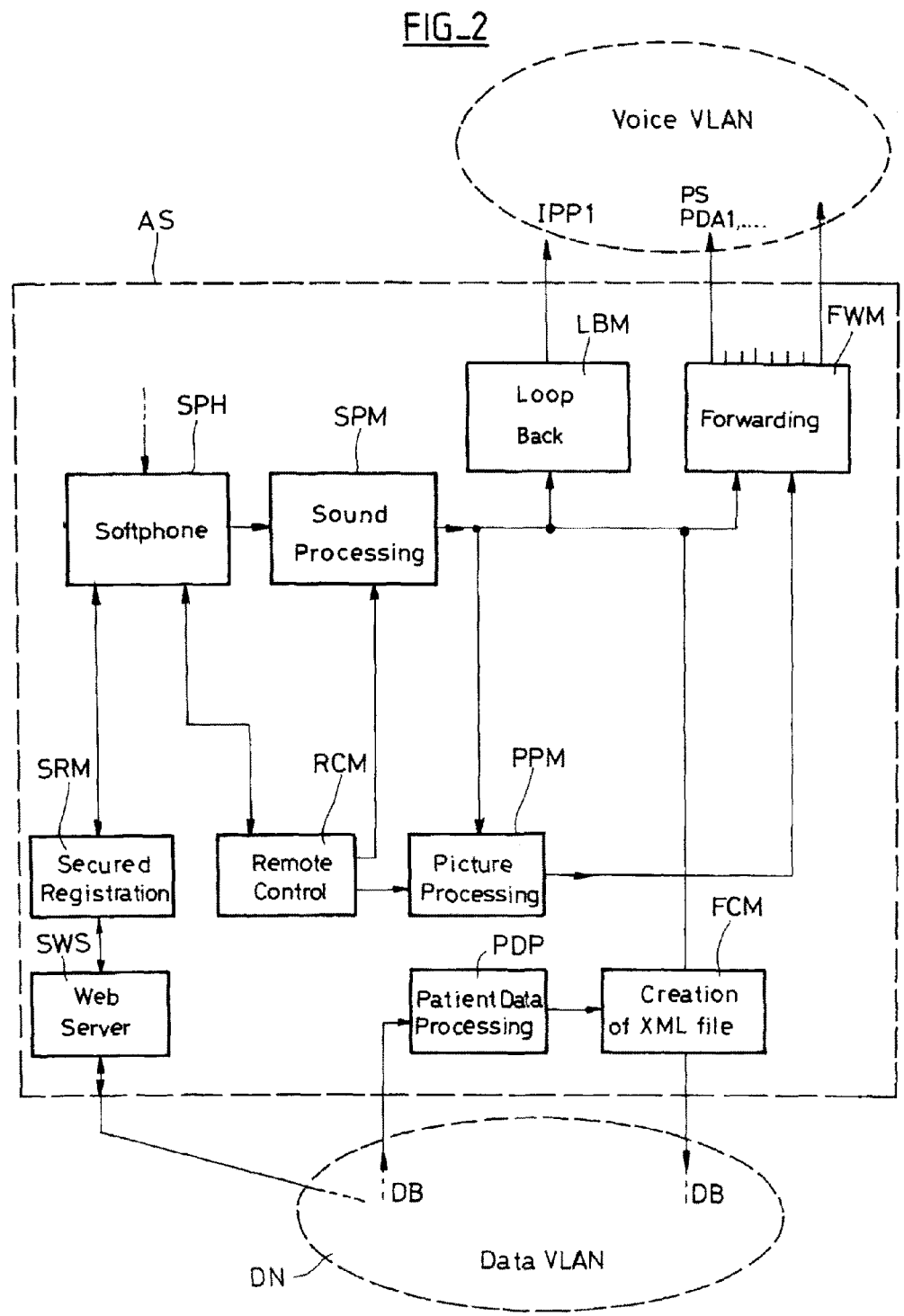
FIG. 2 is a block diagram showing an exemplary embodiment of the application server according to the invention.

FIG. 2 is a block diagram showing more details of the exemplary embodiment AS of the application server according to the invention.

This embodiment AS comprises a softphone SPH, i. e. a software program for making telephone calls over an IP network, using a general purpose computer. This softphone SPH enables to access the application server AS via the voice dedicated VLAN, VN. It acts like a specific telephone set connected to the voice dedicated VLAN, VN:

It will automatically accept a voice call, set up from any telephone set inside or outside the hospital network HN.

It will automatically accept a conference call, set up from any telephone set inside or outside the hospital network HN.

It will initiate a secured registration process to identify any caller.

It will terminate adequately the call set up protocol so as to be in a position to establish a voice connection over the voice dedicated VLAN, VN, without any specific requirement, neither from the calling party, nor from the call server CS.

It will automatically return to an idle state when a call is released by the terminal that has set it up.

The application server AS comprises a secured registration module SRM that is a software program module for controlling the access to the application server AS: For instance, when a practitioner is calling from a patient's room with an IP phone, or when a student is requesting to attend an auscultation lesson with a personal digital assistant or a computer. This secured registration module SRM comprises a local database storing a list of the users that are allowed to access to the server AS, along with their logins and passwords. This local database is managed by classical management tools. In a specific embodiment, the local database is a MySQL database, managed through secured remote connection. The Softphone SP handles the list of students that have subscribed to a particular auscultation course. It ensures control of secured connections of all the students that call it.

The application server AS further comprise a secured web server SWS, coupled to the secured registration module SRM, and that enables an access via a data dedicated VLAN, DN, supported by the hospital network HN. The access is then using the Hypertext Transfer Protocol over Secure Socket Layer (HTTPS).

The application server AS further comprises a remote control module RCM that is a software program module that collaborates with the softphone SP for receiving and decoding remote control commands. It is linked to the other modules constituting the application server AS for controlling them. When voice paths are established over the hospital network HN, inside the voice dedicated VLAN, VN, the application server AS can receive remote control commands sent by a distant terminal for performing several operations that are needed for making an auscultation, for an auscultation lesson, etc. For instance: selecting a parameter for filtering the auscultation sounds, starting/stopping the recording of the auscultation signal, etc. . . .

The application server AS further comprises a sound processing module SPM, that is a software program module for:
  receiving packets containing samples of the auscultation signal, supplied by the softphone SPH,
  de-encapsulating a packet containing samples of the auscultation signal, at the real time transport protocol level,
  then processing these samples; for example, filtering the auscultation sound for enhancing some characteristics useful for a diagnostic.

The application server AS further comprises a loop back module LBM to loop back, at the level of the RTP (Real-time Transport Protocol), the physiological signal that it receives from a terminal, the IP phone IPP1 for instance. This loop back module LBM de-encapsulates a data packet, at the level of RTP, and permutes the source address and the destination address. It loops back an incoming RTP channel so as to send auscultation sounds collected by the chestpiece of the stethoscope ES, back to the headset of this stethoscope ES, via the IP phone IPP1 at the patient's bedside. This enables a practitioner to listen to enhanced auscultation sounds in a quasi real-time operation (Quasi real-time meaning the roundtrip delay over the voice dedicated VLAN, VN, between the IP phone inside the patient's room and the softphone SPH of the application server AS. Ideally, the roundtrip delay should be maintained low enough to avoid disturbance to a practitioner).

The application server AS further comprises a forwarding module FWM that makes n unicasts of an incoming RTP flow directly to n outgoing RTP flows towards the respective terminals of n students, for instance. It can also forward a series of pictures, supplied by the picture processing module PPM, to a terminal, or several terminals, that cannot elaborate such pictures, for instance the IP phone IPP1 at the patient's bedside. The list of students that are authorized to participate to a series of lessons is handled through the local database of the secured registration module SRM.

The application server AS further comprises a picture processing module PPM receiving the processed auscultation sounds from the sound processing module SPM for periodically elaborating pictures (of a phonocardiogram for instance) that will be sent over UDP (User Datagram Protocol), to be displayed on the screen of a terminal that cannot elaborate such pictures, for instance the IP phone IPP1 at the patient's bedside.

The application server AS further comprises a module PDP for processing patient data. It can retrieve, in the database DB, data concerning a patient and/or a practitioner, either for dispatching them to a terminal, or to create, in the application server AS, a new file to be stored into the patient database DB, or directories.

The application server AS further comprises a module FCM for elaborating a file comprising a physiological signal and data related to a patient, and which is adapted for storing in the database DB. In a preferred embodiment, it elaborates an XML file comprising a series of samples of a physiological signal (the auscultation sounds for instance) together with textual data, such as comments provided by the practitioner (at least the location where the sounds have been collected), and administrative data related to the patient and the practitioner. Some of these data can be supplied by the module PDP for processing patient data. Then this XML file is sent over the data dedicated VLAN, DN, to be stored into the patient database DB.

Figure 3:
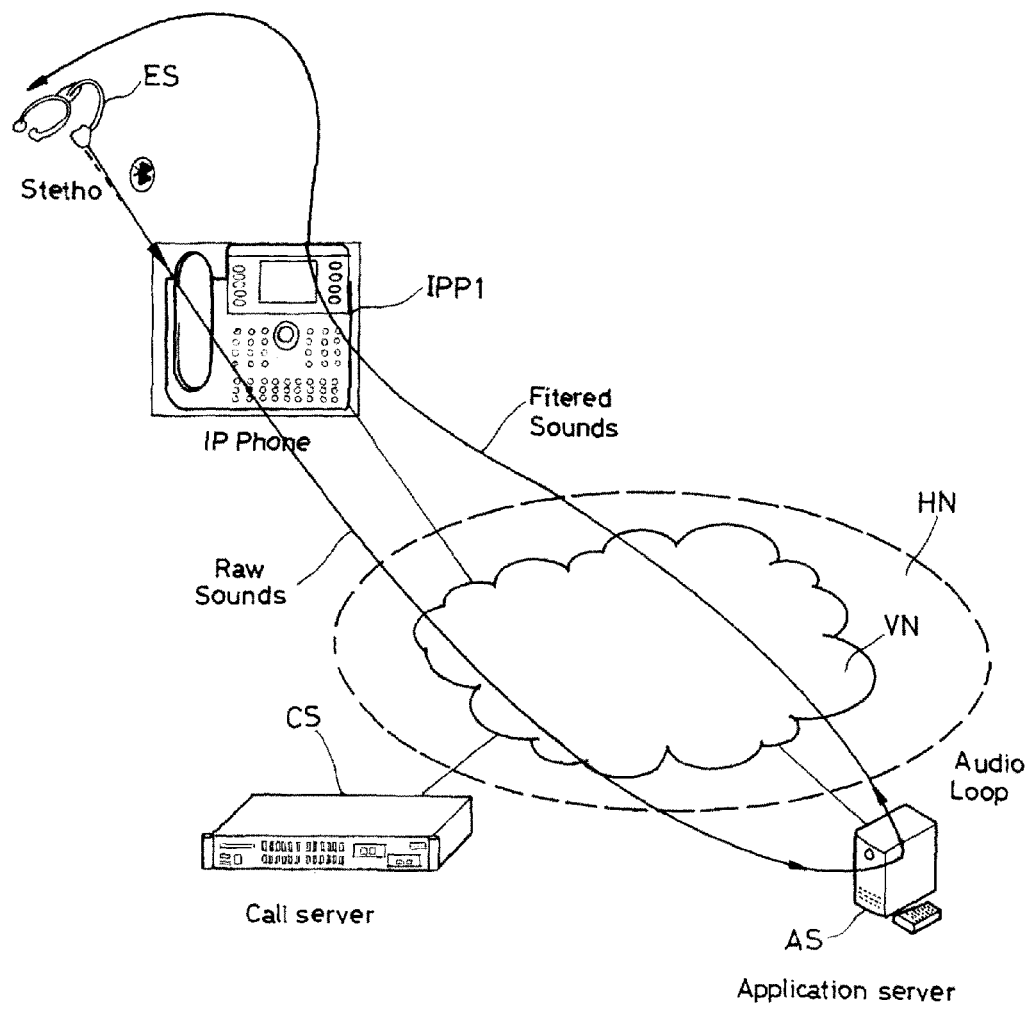
FIG. 3 illustrates the use of this embodiment of the application server for processing auscultation sounds, and then forwarding them back to a stethoscope, in order to enhance sound characteristics that are valuable for a diagnostic.

FIG. 3 illustrates the use of the application server AS for processing raw auscultation sounds collected by the electronic stethoscope ES, and then forwarding filtered auscultation sounds back to the electronic stethoscope ES, in order to enhance sound characteristics that are valuable for a diagnostic. The electronic stethoscope ES is designed so that the auscultation signal can be switched to the IP phone IPP1 instead of the headset of the stethoscope ES, and so that an enhanced auscultation signal supplied by the IP phone IPP1 can be switched to the headset of the stethoscope ES. So an auscultation signal can be sent to the application server AS, via the voice dedicated VLAN, VN, for processing, then be sent back, via the voice VLAN VN, to the ears of the user of the stethoscope ES and possibly dispatched to other terminals connected to the voice dedicated VLAN, VN.

The practitioner connects the stethoscope ES to the Bluetooth interface of the IP phone IPP1 in the classical way. Then the practitioner dials an extension number that designates the application server AS. The call is established by the call server CS in a classical way. The call set up is performed, based on that specific protocol currently used by the call server that is used inside the hospital. This specific call set up procedure becomes more and more SIP based, but proprietary protocols can also be used.

The softphone SPH which is running inside the application server AS behaves like a normal phone, regardless of the evolution of a call (transfer, second call, call transfer, call park, call pick up, etc): When the IP phone IPP1, for instance, calls the application server AS, the call server CS invites the softphone SPH of the application server AS to a call. The softphone SPH accepts the call.

When the call has been set up, the sound processing module SPM, in the application server AS, processes the received auscultation signal. Then the loop back module LBM of the application server AS sends the processed auscultation signal back to the calling terminal. In the present case, the auscultation signal is filtered and then sent back to the IP phone IPP1, and up to the headset of the stethoscope ES, via the Bluetooth link.

The processing by the application server AS can be far more sophisticated than the processing made inside the electronic stethoscope ES, because the processing power of the application server is far greater. Examples of sophisticated filtering methods can be found in the followings documents:

Acoustic echo and noise control A practical approach, Authors: HÄNSLER Eberhard, SCHMIDT Gerhard, WILEY Editor.

IEEE SIGNAL PROCESSING LETTERS, VOL. 11, NO. 4, APRIL 2004, A Fast Converging Algorithm for Network Echo Cancellation, Mehran Nekuii, Student Member, IEEE, and Mojtaba Atarodi, Member, IEEE.

Figure 4:
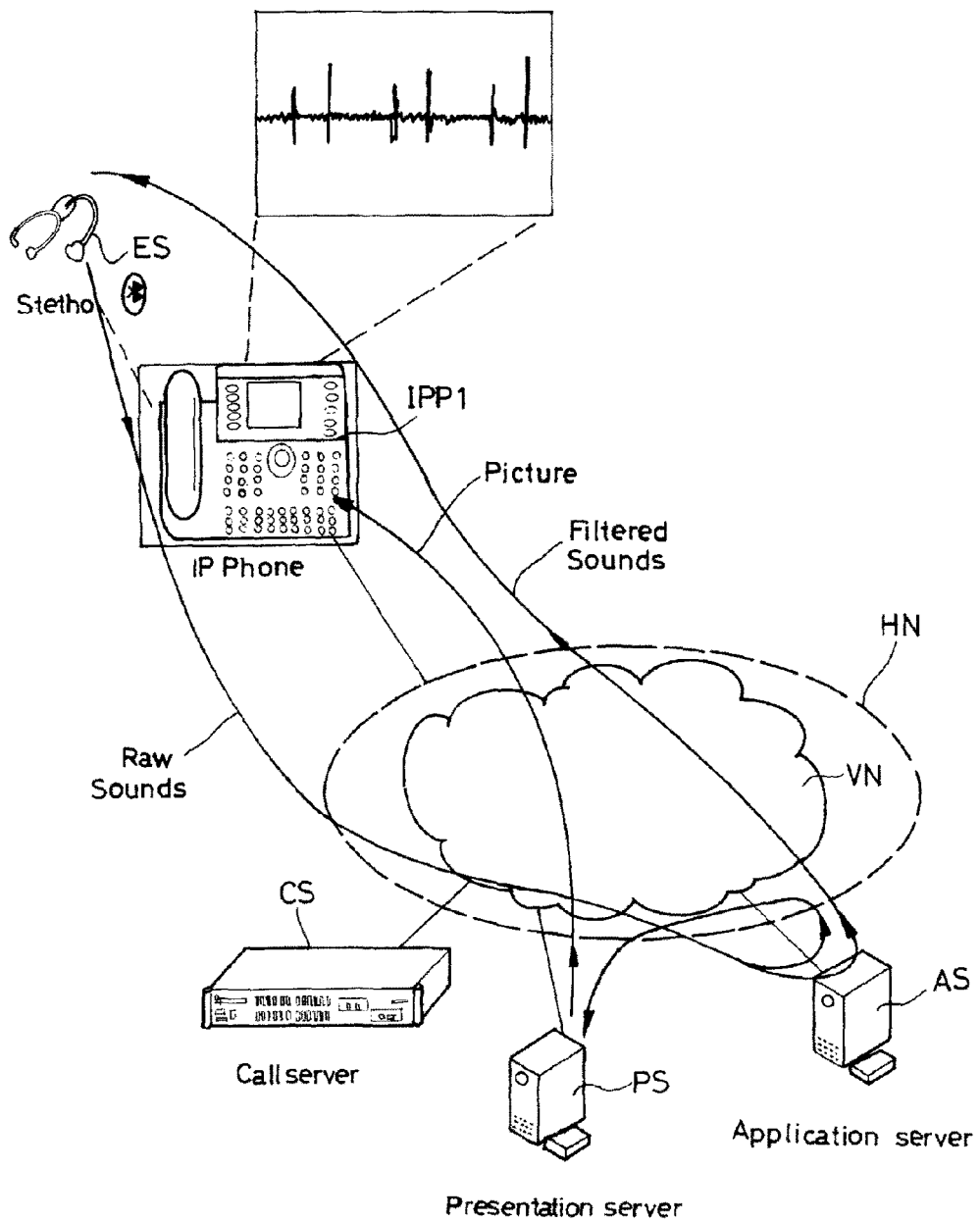
FIG. 4 illustrates the use of this embodiment of the application server for displaying a phonocardiogram on the screen of an IP phone placed at the patient's bedside.

FIG. 4 illustrates the use of the application server AS for displaying a phonocardiogram on the screen of the IP phone IPP1, at the patient's bedside, while sending filtered auscultation sounds to the headset of the stethoscope ES.

The presentation server PS manages the screen and the keyboard of the IP phones of the hospital network HN for several applications that can be exploited via the IP phones. For instance, the screen and the keyboard of the IP phone IPP1 can be used for making an auscultation and for taking a phone call, at the same time. The presentation server PS generates the pictures to be displayed on the screen of the IP phone IPP1 according to the applications being currently used. In the opposite direction, the presentation server PS receives signaling messages from the IP phone IPP1, these messages corresponding to the keys that are pressed, and it forwards them to an appropriate application, in particular to the applications run on the application server AS.

For instance, if the practitioner press a key dedicated to start auscultation, the presentation server PS sends a request to the call server CS to set up a call between the IP phone IPP1 and the application server AS dealing with auscultation. When the application server AS has accepted the call, the presentation server PS then generates an updated picture to be displayed on the screen of the IP phone IPP1. This picture may comprise keywords or icons located near keys of the IP phone IPP1, and that can be dynamically assigned to peculiar functions depending of the applications currently used. When the practitioner presses a key, the presentation server PS receives a message indicating that this key has been pressed. It forwards the message to an appropriate application. If the message concerns a key dedicated to the auscultation, the message is forwarded to the remote control module RCM of the application server AS dealing with auscultation.

The application server AS processes the auscultation signal for continuously generating a sliding waveform in real time. A method for such processing is described in the document U.S. Pat. No. 5,025,809 incorporated here by reference. However the IP phone IPP1 has not enough resources to continuously calculate and display the streaming video corresponding to such a waveform.

The picture processing module PPM of the application server AS elaborates a curve that is the visual representation of the analogue signal corresponding to the auscultation sounds, and then takes periodic pictures of the curve. It forwards the series of pictures to the presentation server PS for displaying these pictures on the screen of the IP phone IPP1. The logical distinction between the two functions (Application server AS and presentation server PS) is a functional split only. Both applications may run on the same machine.

The presentation server PS continuously receives pictures of the curve generated by the application server AS in real time. Theses pictures are transported from the application server AS to the presentation server PS via a VLAN supporting data (not represented on the figure) supported by the hospital local area network HN.

The presentation server PS refreshes the picture displayed on the screen of the IP phone IPP1, via the voice dedicated VLAN, VN, with a rate that is appropriate for the performance of the IP phone IPP1. As an example, a refresh rate of one picture per second, is adequate to provide a good compromise between processing load, network load, and visual comfort during auscultation. The files representing these pictures are compressed. The picture rate and the compression rate are compatible with the limited bandwidth of the connection to the IP phones, and with the limited bandwidth of the displaying means of the IP phones, in order that the pictures can be displayed in real time. Each picture is a kind of photograph of the auscultation signal, compressed with the classical JPEG format as an example, by the picture processing module PPM of the presentation server AS.

Figure 5:
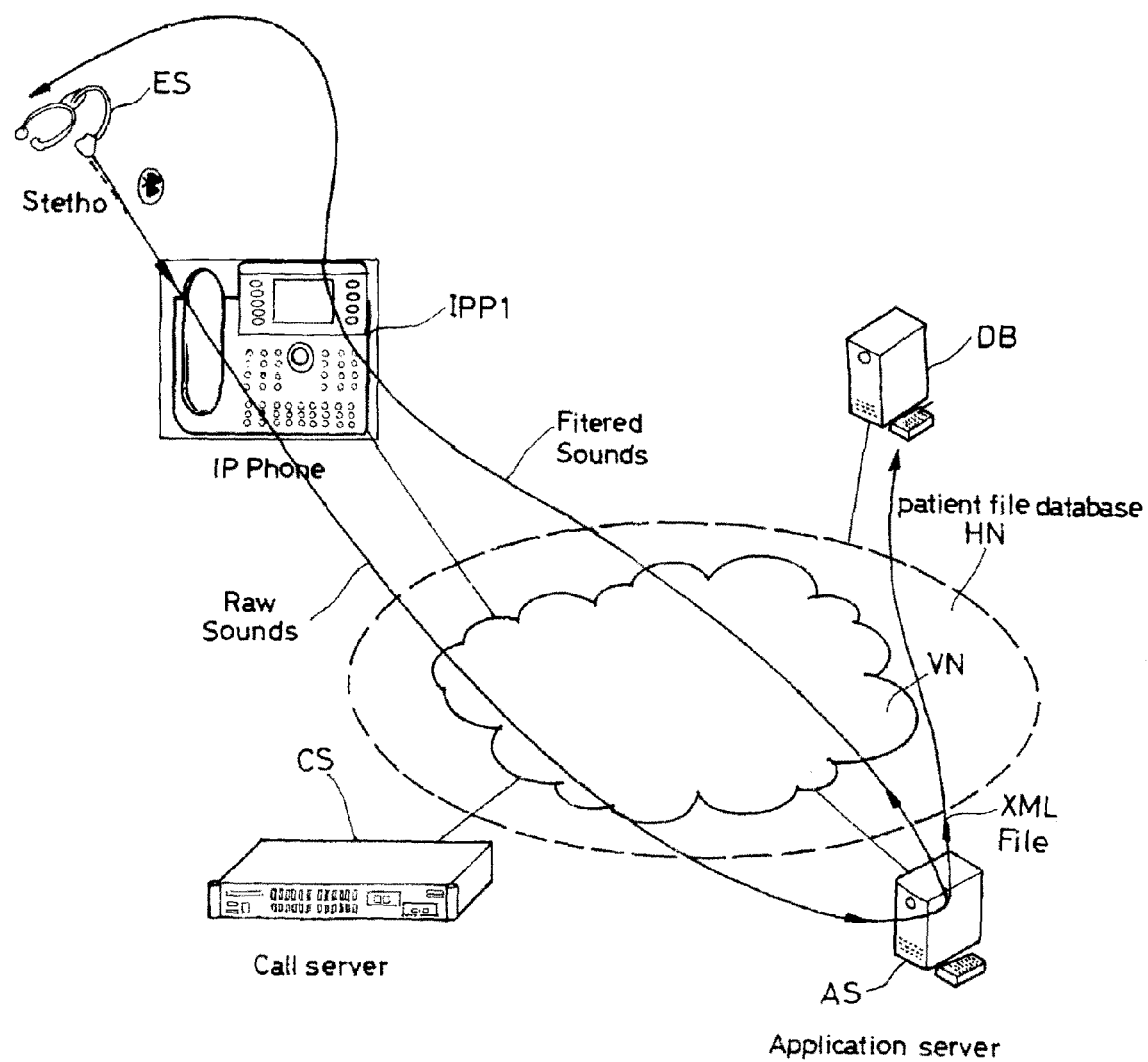
FIG. 5 illustrates the use of this embodiment of the application server for dispatching a processed auscultation signal into a patient's file, in a database.

FIG. 5 illustrates the use of the application server AS for dispatching a processed auscultation signal into a patient's file, in the database DB.

The IP phone IPP1 is in communication with the application server AS via the presentation server PS, as explained above. The secured registration module SRM of the application server AS received the extension number of the IP phone IPP1 when the practitioner was calling. It also received the practitioner's name when he/she logged in.

The practitioner presses some keys of the IP phone IPP1 to command the application server AS to start the recording of the auscultation signal in the sound processing module SPM. The presentation server PS forwards, to the application server AS, the signaling messages indicating what keys have been pressed.

Later the practitioner presses some keys of the IP phone IPP1 to command the application server AS to stop the recording of the auscultation signal in the sound processing module SPM. Then the practitioner presses some keys of the IP phone IPP1 to document the auscultation sound recorded in the sound processing module SPM. In particular, he/she indicates the auscultation zone by pressing keys or moving a navigation button, on the IP phone IPP1. Then the practitioner presses some keys to command the application server AS to store the sound record and annexed information into the patient file database DB.

The file creation module FCM of the application server AS makes an XML file containing:
- The auscultation sound record, in .wav file for instance.
- The extension number of the IP phone IPP1, that will enable to retrieve the room number and the patient's name.
- The practitioner's name.
- The auscultation zone.
- Textual comments.

Then the application server AS sends this XML file to the database DB, via a data dedicated local area network (not represented on the figures) supported by the hospital network HN.

This information can be retrieved later via the web server of the patient file database DB and the application server AS. A user who has an appropriate access right for consulting a patient file and who has an IP terminal connected to the voice dedicated VLAN, VN, calls the softphone SPH of the application server AS. The user accesses to the patient file database DB via the secured registration module SRM of the application server AS. An XML file is read in the database DB and then is sent to the patient data processing module PDP of the application server AS. This latter opens the XML file extracts the auscultation sounds and sends them to the terminal of the requesting user, via the voice dedicated VLAN, VN. It also extracts the textual comments but it does not send them directly to the terminal. It sends them to the presentation PS in order to adapt their format to the display capacity of the destination terminal. Then the presentation PS sends the textual data to the terminal via the voice dedicated VLAN, VN.

The auscultation sounds can also be retrieved to be listened to during an auscultation lesson.

Figure 6:
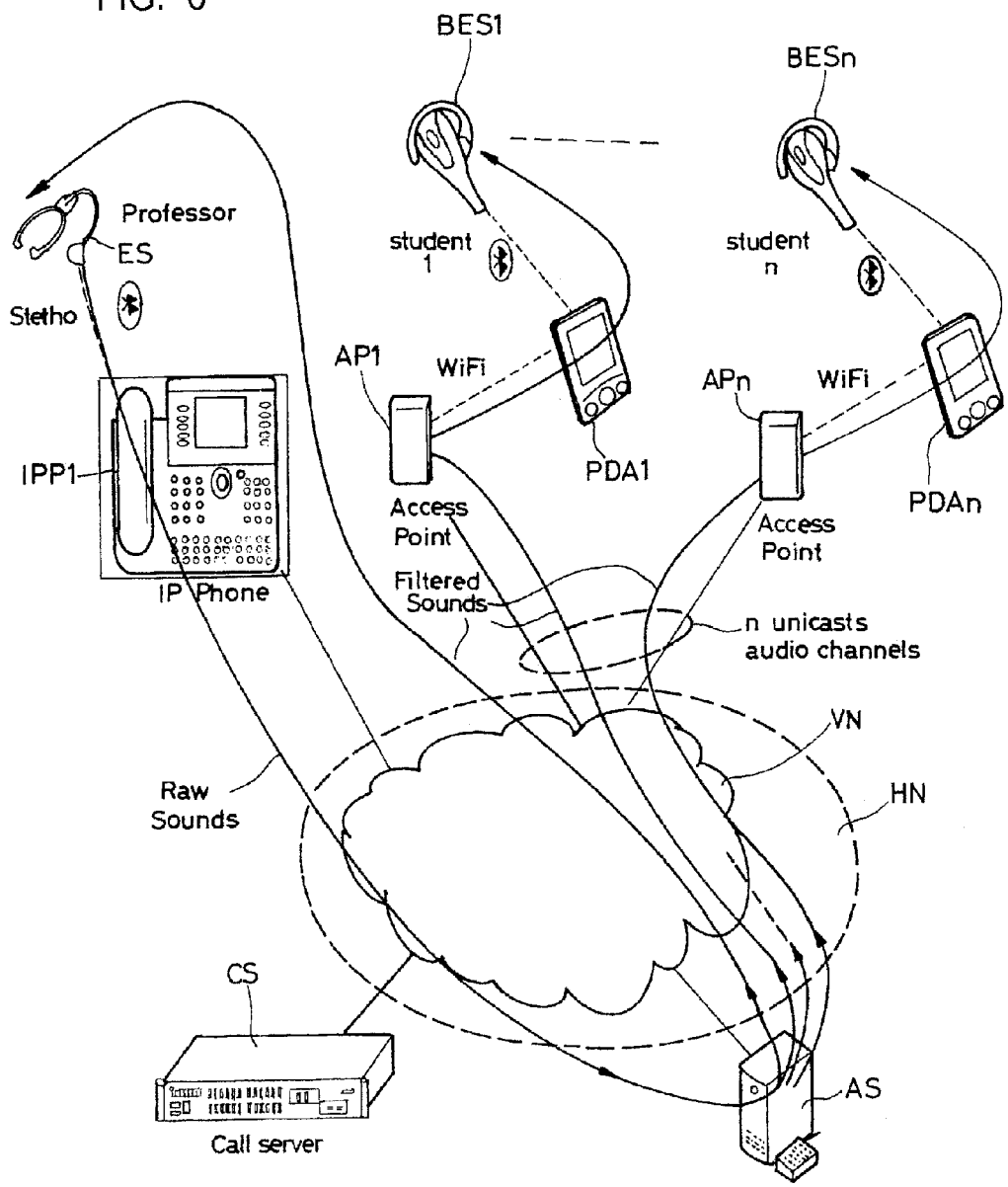
FIG. 6 illustrates the use of this embodiment of the application server for dispatching an auscultation signal to several students during an auscultation lesson.

FIG. 6 illustrates the use of the application server AS to dispatch an auscultation signal to several students for teaching auscultation. An experienced practitioner is in the patient's room and has connected his/her electronic stethoscope ES to the voice dedicated VLAN, via the IP phone IPP1, as explained above.

Students 1, . . . , n are located in several rooms distant from the patient's bedroom, or in the patient's room, and these students will attend an auscultation lesson given by the experienced practitioner. They have digital personal assistants PDA1, . . . , PDAn, that can be connected to the hospital local area network HN, via Wi-Fi access points AP1, . . . , APn respectively. Each digital personal assistant PDA1, . . . , PDAn can be linked to a Bluetooth ear set BES1, . . . , BESn via a Bluetooth interface.

For instance, the student 1 activates his personal digital assistant PDA1 and his/her Bluetooth ear set BES1. The personal digital assistant PDA1 is connected to the hospital network HN by an access point AP1. It comprises a classical web browser that can use the Hypertext Transfer Protocol over Secure Socket Layer (HTTPS).

The personal digital assistant PDA1 does not need a softphone to access to the application server AS because it does not request any phone call setup made by the call server. It simply needs a RTP stack so as to be able to play the auscultation sounds collected from RTP over IP, back to a loudspeaker embedded in the personal digital assistant PDA1, or to the Bluetooth ear set BES1.

Firstly, the student 1 connects the personal digital assistant PDA1 directly to the secured web site SWS of the application server AS, this web site being dedicated to the access control, and using the Hypertext Transfer Protocol over Secure Socket Layer (HTTPS). The secured web site SWS answers with a prompt requesting a login and a password. The student 1 logs in, gives a password, and requests to attend the current auscultation lesson. The application server AS checks with the secured registration module SRM whether the student has a right to access this course, by consulting a list of students who have subscribed to this course.

If the student 1 has a right to access, the application server AS extracts the IP address of the personal digital assistant PDA1 from the previously received messages. Then it creates a RTP flow to the personal digital assistant PDA1, by sending RTP packets containing this IP address as a destination address, via the voice dedicated VLAN, VN. It sends auscultation signal packets on this RTP flow. These packets are copies of the processed auscultation signal packets that the application server AS sends back to the IP phone IPP1.

The web browser of the personal digital assistant PDA1 receives this RTP flow and detects its own IP address is the destination addresses of the packets in this RTP flow.

n students can request simultaneously for attending the same auscultation lesson. The application server AS does not establish a multicast link to the n students, but it establishes n unicast RTP links by generating n copies of the RTP flow that constitutes the processed auscultation signal that the application server AS sends back to the IP phone IPP1.

So there is no multicast (forbidden in most cases by the security means of the hospital network HN) but n unicasts that are accepted by the hospital network HN. The forwarding module FM of the application server AS generates n copies of each processed packet and then modifies their respective destination IP addresses, by replacing the IP address of the application server AS, by the respective IP addresses of the personal digital assistants PDA1, . . . , PDAn of the n students. Then it re-encapsulates the n copies at the RTP level, and respectively forwards them to the personal digital assistant PDA1, . . . , PDAn via the voice dedicated VLAN, VN.

FIG. 7 illustrate the use of the application server AS for displaying a phonocardiogram on a student's personal digital assistant PDA1 during the auscultation lesson. This personal digital assistant PDM receives an auscultation sound from the application AS, via the voice dedicated VLAN, VN, as explained with reference to FIG. 6. This personal digital assistant PDA1 runs a picture processing module similar to the picture processing module PPM run on the application server AS for elaborating a curve that is the visual representation of the analogue signal corresponding to the auscultation sound. Then it displays, on the screen of the personal digital assistant PDA1, a phonocardiogram similar to the one displayed on the screen of the IP phone IPP1.

This personal digital assistant PDA1 has a processing power much greater than the processing power of an IP phone, so it does not need the application server AS and the presentation server PS to generate and display a phonocardiogram, from the processed auscultation signal received from the application server. The signal processing software running in the personal digital assistant PDA1 may customize the signal that is played back to the ears of the student, based on preferred characteristics defined for this particular student. In addition, a sound recording software program can be run in the personal digital assistant PDA1 to record, on it, the auscultation signal along with oral comments spoken by the student or the professor.

FIG. 8 illustrates the use of the application server AS for consulting a second experienced practitioner during the auscultation lesson. A first practitioner is auscultating a patient with the electronic stethoscope ES, and is listening to the processed auscultation sound sent back by the application server AS. Students, student 1 for instance, may be attending an auscultation lesson delivered by this first practitioner, as described with reference to FIG. 7.

Now the first practitioner wants to get the opinion of a second experienced practitioner who is located in the same hospital for instance. The first practitioner calls the IP phone IPP2 of the second practitioner, by using the keyboard of the IP phone IPP1, which enables to put a phone call while being connected to the application server AS for sending an original auscultation signal and receiving a processed auscultation signal. The second practitioner takes the call.

Then the first practitioner creates a call conference by classically using the keyboard of the IP phone IPP1, to enable the second practitioner to listen to the processed auscultation signal, and to see the phonocardiogram on the screen of the IP phone IPP2 as it is on the screen of the IP phone IPP1.

If the second practitioner is outside the hospital network, and if he/she has a personal computer or a personal digital assistant that runs the a picture processing module similar to the picture processing module PPM run on the application server AS, then he/she can watch a phonocardiogram similar to the one displayed on the screen of the IP phone IPP1.

There is claimed:

1. An application server that dispatches physiological signals in a hospital, in real time, the hospital comprising a local area network infrastructure with a virtual local area network supporting a voice over IP telephony application, said server comprising:
    a soft phone that receives packets containing samples of a physiological signal via a first terminal connected to the virtual local area network,
    a sound processing module that de-encapsulates a received packet containing samples of said physiological signal, at the real time transport protocol level, and
    a loop back module that creates a second packet containing samples of said physiological signal, and forwards the second packet back at least to the first terminal.

2. The application server according to claim 1, wherein the sound processing module processes the samples of the received physiological signal; and the loop back module inserts, into the second packet, processed samples supplied by said sound processing module.

3. The application server according to claim 1, wherein the loop back module creates a source address and a destination address by permuting the source address and the destination address of said first packet, at the real time transport protocol level.

4. The application server according to claim 1, further comprising a forwarding module that creates a third packet containing samples of said first packet, and forwards the third packet to at least a second terminal connected to the virtual local area network, by creating a point to point flow for each destination terminal.

5. The application server according to claim 4, wherein the sound processing module processes the samples of the received physiological signal; and said forwarding module inserts, into the third packet, processed samples supplied by said sound processing module.

6. The application server according to claim 4, wherein said forwarding module creates a source address by extracting a destination address of the first packet, and creates a destination address by taking an address of the second terminal, at the real time transport protocol level.

7. The application server according to claim 1, further comprising a picture processing module that builds a series of still images that represents physical characteristics of the physiological signal, and sends each image over a user datagram protocol to at least a terminal connected to the virtual local area network.

8. The application server according to claim 1, further comprising a module that elaborates a file comprising a physiological signal and data related to a patient, and which is adapted for storing in a data base.

9. The application server according to claim 1, wherein the softphone is further operative to:
    accept a phone call;
    accept a conference call;
    terminate adequately a call set up protocol so as to be in a position to establish a voice connection over the virtual local area network, without any specific requirement, neither from a calling party, nor from a call server; and
    return to an idle state when a call is released by the terminal that has set it up.

10. A method for dispatching physiological signals in real time via a local area network infrastructure including a virtual local area network supporting a voice over IP telephony application; said method comprising:
    receiving packets containing samples of a physiological signal via a first terminal connected to the virtual local area network;
    de-encapsulating the received packet containing samples of said physiological signal at a real time transport protocol level; and
    creating a second packet containing samples of said physiological signal, and forwarding the second packet back at least to the first terminal.

* * * * *